US008802389B2

(12) United States Patent
Adang et al.

(10) Patent No.: US 8,802,389 B2
(45) Date of Patent: Aug. 12, 2014

(54) **IDENTIFICATION OF TOXIN-BINDING PROTEIN INVOLVED IN RESISTANCE TO *CRY1* TOXINS, AND RELATED SCREENING METHODS**

(75) Inventors: Michael J. Adang, Athens, GA (US); Rebecca McNall, Athens, GA (US); Juan Luis Jurat Fuentes, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 267 days.

(21) Appl. No.: 13/274,646

(22) Filed: Oct. 17, 2011

(65) Prior Publication Data

US 2012/0034610 A1 Feb. 9, 2012

Related U.S. Application Data

(62) Division of application No. 10/897,621, filed on Jul. 23, 2004, now Pat. No. 8,039,229.

(60) Provisional application No. 60/490,119, filed on Jul. 25, 2003.

(51) Int. Cl.
*A01N 25/00* (2006.01)
*C12N 1/20* (2006.01)
*C12Q 1/00* (2006.01)
*C12Q 1/02* (2006.01)
*C12Q 1/42* (2006.01)
*G01N 33/53* (2006.01)
*G01N 33/554* (2006.01)
*G01N 33/567* (2006.01)
*G01N 33/569* (2006.01)

(52) U.S. Cl.
USPC ............... 435/21; 424/405; 435/4; 435/7.2; 435/7.8; 435/7.9; 435/7.21; 435/7.32; 435/29; 435/252.5; 435/832; 435/962; 435/967; 435/970

(58) Field of Classification Search
None
See application file for complete search history.

(56) References Cited

U.S. PATENT DOCUMENTS

| | | | |
|---|---|---|---|
| 5,695,928 A | 12/1997 | Stewart et al. | |
| 5,723,304 A | 3/1998 | Abuknesha | |
| 7,385,107 B2 | 6/2008 | Donovan et al. | |
| 2005/0064386 A1 | 3/2005 | Adang et al. | |

OTHER PUBLICATIONS

Leigh et al, "Delta Endotoxin Inhibits a Phosphatase in Midgut Epithelial Membranes of *Heliothis virescens*", Insect Biochem. vol. 19, No. 2, pp. 145-152, 1989.*
English et al., "Delta endotoxin inhibits a phosphatase in midgut epithelial membranes of *Heliothis virescens*," Insect Biochemistry (1989), p. 145-152, vol. 19, No. 2.
Jurat-Fuentes et al., "Characterization of a Cry1Ac-receptor alkaline phosphatase in susceptible and resistant . . . ," European J. Biochem. (2004), p. 3127-3135, vol. 271, No. 15.
Banks, D.J. et al., "*Bacillus thuringiensis* Cry1Ac and Cry1Fa delta-endotoxin binding to a novel 110 kDa . . . ," Insect Biochem, Molec. Biol., 2001, pp. 909-918, vol. 31.
Burton, S.L. et al., "N-acetylgalactosamine on the putative insect receptor aminopeptidase N is recognized by a site . . . ," J. Mol. Biol., 1999, pp. 1011-1022, vol. 287.
Cerneus, D. et al., "Detergent insolubility of alkaline phosphatase during biosynthetic transport and endocytosis," J. Biol. Chem., 1993, pp. 3150-3155, vol. 268.
Chang, W. et al., "Expression of epithelial alkaline phosphatase in segmentally iterated bands during grasshopper limb morphogenesis," Development, 1993, pp. 651-663, vol. 118.
Derbyshire, D.J. et al., "Crystallization of the *Bacillus thuringiensis* toxin Cry1Ac and its complex . . . ," Acta Crystallogr. D Biol. Crystallogr., 2001, pp. 1938-1944, vol. 57.
Fukushima, K. et al., "A (beta)-N-Acetylglucosaminyl Phosphate Diester Residue is Attached . . . ," J. Biol. Chem., 2003, pp. 36296-36303, vol. 278.
Gahan, L.J. et al., "Identification of a gene associated with Bt resistance in *Heliothis virescens*," Science, 2001, pp. 857-860, vol. 293.
Garczynski, S.F. et al., "Identification of putative insect brush border membrane-binding molecules specific . . . ," Appl. Environ. Microbiol., 1991, pp. 2816-2820, vol. 57.
Griffitts, J.S. et al., "Resistance to a bacterial toxin is mediated by removal of a conserved glycosylation pathway . . . ," J. Biol. Chem., 2003, pp. 45594-45602, vol. 278.
Hoffman, C. et al., "Specificity of *Bacillus thuringiensis* delta-endotoxins is correlated with the presence . . . ," Proc. Natl. Acad. Sci. USA, 1988, pp. 7844-7848, vol. 85, No. 21.
Itoh, M. et al., "Cloning of soluble alkaline phosphatase cDNA and molecular basis of the polymorphic nature . . . ," Insect Biochem. Molec. Biol., 1999, pp. 121-129, vol. 29.
Jurat-Fuentes, J.L. et al., "Importance of Cry1 delta-endotoxin domain II loops for binding specificity in Heliothis . . . ," Appl. Environmen. Microbiol., 2001, pp. 323-329, vol. 67.

(Continued)

*Primary Examiner* — Debbie K Ware
(74) *Attorney, Agent, or Firm* — Faegre Baker Daniels LLP (57) ABSTRACT

The subject invention relates in part to the surprising and unexpected discovery that insects that are resistant to *Bacillus thuringiensis* Cry toxins have measurably altered alkaline phosphatase (ALP) activity as compared to insects that are susceptible to Cry toxins. This and other surprising discoveries reported herein have broad implications in areas such as managing and monitoring the development of insect resistance to B.t. toxins. For example, the subject invention provides a simple and fast assay (enzymatic or otherwise) for detecting ALP activity levels and thereby monitoring the development of resistance by insects to crystal protein insect toxins. There was no prior motivation or suggestion to go about resistance monitoring using this simple and easy approach.

12 Claims, 3 Drawing Sheets

(56) References Cited

OTHER PUBLICATIONS

Jurat-Fuentes, J.L. et al., "Altered Glycosyiation of 63- and 68-kilodalton microvillar proteins in Heliothis . . . ," Appl. Environ. Microbiol., 2002, pp. 5711-5717, vol. 68.

Lee, M.K. et al., "Identification of residues in domain III of *Bacillus thuringiensis* Cry1Ac toxin . . . ," Appl. Environ. Microbiol., 1999, pp. 4513-4520, vol. 65, No. 10.

Lee, M.K. et al., "Resistance to *Bacillus thuringiensis* Cry1A d-endotoxins in a laboratory-selected Heliothis . . . ," Appl. Environ. Microbiol., 1995, pp. 3836-3842, vol. 61.

Lee M.K. et al., "Location of a Bombyx mori receptor binding region on a *Bacillus thuringiensis* delta-endotoxin," J. Biol. Chem., 1992, pp. 3115-3121, vol. 267, No. 5.

Luo, K. et al., "Toxicity, binding and permeability analyses of four *Bacillus thuringiensis* Cry1 d-endotoxins . . . ," Appl. Environ. Microbiol., 1999, pp. 457-464, vol. 65.

McNall, R.J. et al., "Identification of novel *Bacillus thuringiensis* Cry1Ac binding proteins in *Manduca sexta* . . . ," Insect Biochem, Molec. Biol., 2003, pp. 999-1010, vol. 33.

Mohammed, S.I. et al., "Altered binding of the Cry1Ac toxin to larval membranes but not to the toxin-binding . . . ," Appl. Environ. Microbiol., 1996, pp. 4168-4173, vol. 62, No. 11.

Oltean, D.I., et al., "Partial purification and characterization of *Bacillus thuringiensis* Cry1A toxin receptor a . . . ," Appl. Environ. Microbiol. 1999, pp. 4760-4766, vol. 65.

Sangadala, S. et al., "Carbohydrate analyses of *Manduca sexta* aminopeptidase N, co-purifying . . . ," Insect Biochemistry and Molecular Biology, 2001, pp. 97-107, vol. 32, No. 1.

Sangadala, S. et al., "A mixture of *Manduca sexta* aminopeptidase and phosphatase enhances *Bacillus thuringiensis* . . . ," J. Biol. Chem., 1994, pp. 10088-10092, vol. 269.

Van Rie, J. et al., "Receptors on the brush border membrane of the insect midgut as determinants of the specificity . . . ," Appl. Environ. Microbiol., 1990, pp. 1378-1385, vol. 56.

Whalon, M.E., et al., "Bt: Mode of action and use", Arch. Insect Biochem. Physiol., 2003, pp. 200-211, vol. 54.

Zhuang, M. et al., "*Heliothis virescens* and *Manduca sexta* lipid rafts are involved in Cry1A toxin binding to the midgut . . . ," Comp. Biochem. Physiol., 1991, pp. 437-443, vol. 99B.

\* cited by examiner

IDENTIFICATION OF TOXIN-BINDING PROTEIN INVOLVED IN RESISTANCE TO CRY1 TOXINS, AND RELATED SCREENING METHODS

CROSS-REFERENCE TO RELATED APPLICATIONS

This application is a divisional of Ser. No. 10/897,621, filed Jul. 23, 2004, now U.S. Pat. No. 8,039,229, and claims priority to provisional application Ser. No. 60/490,119, filed Jul. 25, 2003.

BACKGROUND OF THE INVENTION

Billions of dollars are spent each year in efforts to control insects that damage crops and threaten food supplies. One alternative to the use of synthetic chemical pesticides are naturally occurring insecticidal crystal protein (Cry) toxins from the bacterium *Bacillus thuringiensis* (B.t.). In order to preserve Cry proteins as a viable option for pest control in years to come, efforts are being made to prevent their overuse, as the development of resistance to Cry proteins by some insect strains has been observed under certain conditions. The two main insects that are currently known to develop resistance to Cry proteins are the diamondback moth (DBM; *Plutella xylostella*) and the tobacco budworm (*Heliothis virescens*).

In understanding how these and other insects might develop resistance to Cry proteins, the mechanism(s) of action of Cry proteins is being investigated. Specific binding to insect midgut receptors is a key step in the mode of action of Cry proteins. Despite exceptions [1], in most cases Cry toxin specificity and potency correlate with the extent of toxin binding to midgut brush border membrane receptors in vitro [2, 3]. Effective toxin binding to receptors results in toxin insertion and oligomerization on the midgut cell membrane, leading to pore formation and cell death by osmotic shock [4].

In brush border membrane vesicles (BBMV) from *Heliothis virescens* larvae, three groups of binding sites (A, B, and C) for Cry1A toxins were proposed based on their toxin binding specificities [5, 6]. The A binding sites, which bind Cry1Aa, Cry1Ab, Cry1Ac, Cry1Fa and Cry1Ja toxins, include the cadherin-like protein HevCaLP (Jurat-Fuentes et al., in preparation) and a 170-kDa N-aminopeptidase (APN) [5, 7-9]. Currently, there is evidence that both HevCaLP [10] and the 170-kDa APN [8, 10] function as Cry1A toxin receptors, and knockout of HevCaLP, a protein predicted to function in cell adhesion processes, results in Cry1 resistance in larvae of YHD2 strains of *H. virescens* [10]. In the B binding site group, a 130-kDa protein has been shown to recognize both Cry1Ab and Cry1Ac. The C binding site group includes Cry1Ac toxin-binding proteins smaller than 100-kDa in size [5].

Cry1 toxin-binding proteins of 60- to 80-kDa in size have been described in toxin overlays of BBMV proteins from *H. virescens* [5], *Manduca sexta* [1], and *Plodia interpunctella* [12]. In 2D proteomic analysis of *M. sexta* BBMV proteins, McNall and Adang [13] reported Cry1Ac binding to a form of alkaline phosphatase (ALP, EC 3.1.3.1). Membrane bound ALP from *Bombyx mori* and *M. sexta* are attached to the brush border cell membrane by a glycosylphosphatidylinositol (GPI) anchor [13-15]. Specific interactions between Cry1Ac and ALPs under native conditions resulting have been reported for *M. sexta* [16] and *H. virescens* [17].

Altered glycosylation of 63- and 68-kDa glycoproteins was proposed as the reason for reduced binding of soybean agglutinin (SBA) in *H. virescens* YHD2 strain, which are resistant to Cry1Ac [11]. However, a correlation between a reduction in the amount of the 68 kDa protein and the development, by insects, of resistance to B.t. Cry proteins was never before suggested or investigated. Furthermore, a link between membrane-bound alkaline phosphatases (and associated levels of enzyme activity) and the development of resistance by insects to Cry proteins has never been proposed or suggested.

BRIEF SUMMARY OF THE INVENTION

The subject invention relates in part to the surprising and unexpected discovery that insects that are resistant to *Bacillus thuringiensis* Cry toxins have measurably altered alkaline phosphatase (ALP) activity as compared to insects that are susceptible to Cry toxins. This and other surprising discoveries reported herein have broad implications in areas such as managing and monitoring the development of insect resistance to B.t. toxins. For example, the subject invention provides a simple and fast assay (enzymatic or otherwise) for detecting ALP activity levels and thereby monitoring the development of resistance by insects to crystal protein insect toxins. There was no prior motivation or suggestion to go about resistance monitoring using this simple and easy approach.

BRIEF DESCRIPTION OF THE FIGURES

FIG. 1: Coomassie blue stained gels show equal protein loading; FIG. 1B: the 68 KdDa protein in BBMV from YHD2 larvae showed reduced soybean agglutinin (SBA) binding; FIG. 1C, the 68 KDa protein was recognized by an anti-mALP sera; FIG. 1D: the 68 KDa protein displayed ALP activity in blots of BBMV proteins; FIG. 1E: the same 68 KDa protein is also recognized by anti-CRD sera, indicating it is GPI-anchored to the BBMV.

FIG. 2 illustrates analysis of oligosaccharides on HvALP by lectin blotting. BBMV proteins from YDK larvae (susceptible larvae) were blotted and probed with specific lectins as indicated in the figure. Lane 1: bound lectins were visualized by enhanced chemiluminescence. Lane 2: immunodetection of HvALP using sera against the mALP form *B. Mori*. Lane 3: competition of lectin binding with the respective hapten sugar. ConA, SBA, and WFL show both lectin binding in Lane 1 and ALP activity in lane 2; Jac, HPL, RCA and DBA show only ALP activity but not lectin binding: PNG-F treated first then SBA binding samples shows ALP activity only, not SBA binding, indicating HvALP's lectin binding relies on terminal GalNac. The rest of lectins GSL-1 and SJA bound proteins, although similar size to 68 KDa protein, do not show ALP activity in lane.

FIG. 3B: Cry1Ac wild type competes SBA binding to HvALP, but does not affect SBA binding to APN. FIG. 3C: Cry1Ac mutant does not prevent SBA binding to HvALP. FIG. 3D: Cry1Ac ligand blot with 125-I Cry1Ac shows when PNG-F removes N-linked oligosaccharides from HvALP, Cry1Ac binding to HvALP disappears, indicating Cry1Ac binds to N-glycosylated HvALP.

FIG. 4A: Coornassie blue stain of BBMV proteins from different strains. FIG. 4B: Sera recognition of HvALP in BBMV from various strains shows recognition of HvALP in YHD2 (lane 2) is reduced compared to YDK and F1 vesicles, suggesting a reduced ALP level in YHD2. FIG. 4C: Alkaline phosphatase activity is higher in YDK and F1 larvae compared to YHD2 vesicles.

DETAILED DESCRIPTION OF THE INVENTION

The subject invention generally relates, in part, to assays for monitoring the development by insects of resistance to crystal protein insect toxins (Cry proteins), such as Cry proteins from *Bacillus thuringiensis* (B.t.). These assays can be practiced in the form of simple kits that are preferably used in the field to screen for the presence of resistant insects. In preferred embodiments, levels of enzyme activity or amounts of enzyme from gut cell membranes are assessed, relative to the levels and amounts from known susceptible insects, for determining the presence or absence of resistant insects. In further preferred embodiments, the enzyme is an alkaline phosatase. In still further preferred embodiments, the alkaline phosphatase is a receptor that binds a Cry protein.

To provide more context for this invention, it should be noted that it was proposed that changes in glycosylation of 63- and 68-kDa midgut glycoproteins in the tobacco budworm (*Heliothis virescens*) correlated with reduced binding (of SBA) and the development of resistance, by *H. virescens*, to the Cry1Ac toxin from (B.t.). [11]. The subject invention stems in part from the unexpected and surprising findings that this 68-kDa protein from *H. virescens* is a membrane-bound, GPI-anchored form of alkaline phosphatase (ALP). This protein is further identified as a receptor for Cry1Ac. This receptor protein is thus referred to herein as HvALP (for *H. virescens* alkaline phosphatase). HvALP is identified herein as being involved in Cry1Ac toxicity to *H. virescens* larvae. Still further surprising is the discovery, as reported herein, that insect resistance to B.t. toxins correlates to altered levels of activity and/or amounts of membrane-bound ALP. This finding has broad implications for areas such as managing insect resistance to B.t. toxins. For example, the subject invention provides a simple and fast assay (enzymatic or otherwise) for detecting and monitoring the development of resistance by insects to crystal protein insect toxins. There was no prior motivation or suggestion to go about resistance monitoring using this simple and easy approach.

This invention stems in part from the observation that changes in alkaline phosphatase contribute to insects developing resistance to Cry proteins. It was proposed that a specific isoform of alkaline phosphatase binds Cry1Ac, and this receptor is modified in YHD2 resistant larvae (a B.t.-resistant strain of *H. virescens*). The subject invention relates in part from the discovery that HvALP activity is lower in brush border membrane vesicles from the YHD2 strain.

Ligand and lectin blots together with glycosidase digestion assays revealed that the existence of N-linked oligosaccharides containing terminal N-Acetylgalactosamine (GalNAc) residues on HvALP was necessary for Cry1Ac binding. Results reported herein indicate that reduced soybean agglutinin (SBA) binding to HvALP from Cry1Ac resistant larvae was surprisingly attributable to reduced amounts of HvALP in resistant larvae. Immunoblotting and specific alkaline phosphatase activity of BBMV proteins from susceptible and resistant larvae indicated that decreased HvALP levels were produced in YHD2 larvae. Quantification of specific alkaline phosphatase activity in brush border membrane proteins from susceptible (YDK and F1 generation from backcrosses) and resistant YHD2 *H. virescens* larvae confirmed the reduced HvALP levels observation.

Accordingly, the subject invention provides methods for assaying and detecting altered ALP levels (including detecting less ALP activity) in a suitable sample (a membrane preparation from a lepidopteran pest, such as virescens, in preferred embodiments), as compared to ALP levels in non-resistant insects. The presence of an unexpected level of ALP indicates a B.t.-resistant insect. The subject invention provides a simple and fast assay (enzymatic or otherwise) for detecting and monitoring the development of resistance by insects to crystal protein insect toxins. There was no prior motivation or suggestion to go about resistance monitoring using this simple and easy approach.

Prior to the subject invention, it was never suspected or suggested that the reduced binding was due to an alteration to or a reduction in the levels (amount or activity) of the subject ALP receptors. As explained in more detail below, receptors generally serve important cell functions. Thus, one would not have expected, and it was very surprising, to find resistance to be associated with absence or reduction of this receptor. There was no prior motivation to screen, in the context of tracking B.t. resistance, an insect for altered or reduced levels of ALP receptors as discussed in detail herein.

It is interesting to note that in whole-insect brush border membrane vesicle (BBMV) preparations obtained from *Plutella xylostella* (the diamondback moth or DBM), alkaline phosphatase activity was found to be higher in both the homogenate and BBMV of resistant insects compared to susceptible insect strains. In-gel activity assays of SDS-PAGE separated BBMV shows higher activities for both whole-insect and gut BBMV preparations of resistant insects compared to the corresponding susceptible preparations. Without being bound by a specific theory regarding mechanism of action, it is possible that resistant DBM have two forms of ALP, and the B.t. receptor form is "shed" and another non-binding form is present in greater amounts. With this in mind, it is now possible, according to the subject invention, to design antibodies (or other probes), for use in assays discussed herein, that bind specifically (only) to the Cry binding form of ALP (in a particular insect) and not to other forms of ALP.

The initial hypothesis to explain reduced Cry1Ac and SBA binding in YHD2 larvae was based on possible alteration of protein glycosylation in resistant insects [11]. Surprisingly however, presently disclosed results from immunoblotting and alkaline phosphatase activity detection revealed instead that HvALP protein levels were decreased in BBMV from YHD2 larvae. Therefore, decreased SBA binding to HvALP from YHD2 vesicles was presently, and surprisingly, found to be due to reduced protein levels rather than altered glycosylation. Although due to limiting YHD2 materials, oligosaccharide analysis was only performed in BBMV from YDK larvae, hence potential alterations of HvALP glycosylation in YHD2 larvae cannot be completely ruled out. In any case, considering that F1 generation larvae bound Cry1Ac toxin and were only two fold resistant to Cry1Ac [11], the present results show a direct correlation between decreased HvALP levels and increased resistance to Cry 1 Ac. (BBMV from the F1 generation of reciprocal crosses recovered HvALP levels observed for the susceptible parents independently of the sex of the susceptible progenitor, demonstrating autosomal recessive transmission of this trait.) While YHD2 larvae might have multiple resistance mechanisms, what is important is the subject discovery of the link between reduced levels of this 68 kDa protein and resistance, which was never heretofore suggested.

Electrophoretic variations of alkaline phosphatase between different strains or developmental stages have been reported for *Drosophila melanogaster* [54], *Aedes aegypti* [55], and *B. mori* [56, 57], although the physiological consequences of these variations are not clearly understood. In the Tsunomata *B. mori* strain, reduced mALP activity correlated with undetectable levels of mALP antigen, while there were no alterations in gene copy or transcript size [57]. These results suggested that electrophoretic mALP polymorphisms were due to post-transcriptional processes.

Insect alkaline phosphatases have been proposed to function in active absorption of metabolites and transport processes [29], although there is also evidence for participation in cell adhesion and differentiation [59]. According to these important functions, significant fitness costs associated with reduced ALP activity would be expected. Thus, one would not have expected viable insects to develop resistance by eliminating or reducing membrane-associated ALP.

The specific mechanism by which YHD2 larvae reduce HvALP expression can be further investigated. As stated above, if information from *B. mori* mALP could be applied to HvALP, the decreased activity observed in virescens might not be related to changes in gene copy number or transcription. An alternative hypothetical mechanism to reduce receptors in midgut brush border membranes was previously proposed by Lu and Adang [60]. According to this hypothesis, GPI-anchored proteins would be selectively solubilized by endogenous PIPLC digestion in Bt-resistant insects. Such treatment would result in elimination of potential Cry toxin binding sites, such as aminopeptidases, from the midgut epithelium. In support of this hypothesis, *B. mori* mALP is solubilized by midgut epithelium enzymes to form digestive fluid alkaline phosphatase (dALP), which is highly resistant to degradation by midgut proteases [61].

In any case, the subject results demonstrate a direct correlation between decreased HvALP levels and Cry resistance in *H. virescens*. HvALP may be a critical component in toxicity, or alternatively, the reduced HvALP levels observed in resistant larvae may indicate broader alterations in the brush border membrane. One possibility is that resistant larvae have altered membrane components such as lipid rafts that affect the amounts of HvALP localized to the brush border membrane. The specific role of HvALP in Cry1Ac intoxication can be investigated further.

Whatever the exact mechanisms of action are, HvALP is clearly identified herein as a resistance marker, so biochemical and DNA-based tests may now be developed to detect emergence of resistance to B.t. crops in field populations. Sample insects can be collected in many ways from many different locations. The subject invention relates to the discovery that ALP is a membrane receptor for Cry toxins, and insects such as *Heliothios virescens* can evolve resistance to Cry1Ac, for example, by somehow shedding this receptor (i.e., by effectively reducing the amount of this enzyme in their gut/on gut cells). These surprising discoveries have broad implications in areas such as managing insect resistance to B.t. toxins. For example, insects can be screened for the presence or absence of resistance by, for example, isolating membrane proteins and screening them for the presence or absence of the activity associated with ALP. The presence or absence of the activity of this protein can also be screened directly (without first isolating membrane proteins).

As will be recognized in the art in light of the subject disclosure, the subject invention is not limited to screening *Heliothis virescens*. Other insects, including *Plutella xylostella* (diamondback moths) and *Manduca sexta*, can also be screened with methods and apparatuses of the subject invention. Lepidopterans are preferred screening targets, but other insects can also be screened according to the subject invention. In light of the subject discovery, it will now be known that decreased amounts of ALP receptors can be an indicator of insects developing resistance to crystal protein insect toxins.

Furthermore, the subject invention is not limited to Cry1Ac receptors and managing and/or monitoring resistance to Cry1Ac. Resistance to other insect toxin proteins can also be assessed according to the subject invention. Cry1A toxins (such as 1Aa, 1Ab, and 1Ac) are one preferred group of toxins for which the development of resistance thereto can be monitored according to the subject invention. Other Cry proteins are identified in "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean, *Microbiology and Molecular Biology Reviews* (1998) Vol 62:807-813. It is also available online.

Detecting decreased (or altered) levels of ALP in an insect's gut, gut membrane, and/or gut cell membranes can be done in a variety of ways. One way is by detecting ALP enzymatic activity in a suitable activity. Antibodies (monoclonal or polyclonal) to ALP can also be used in detection methods. Methods such as ELISA are well-known in the art. Antibodies can also be linked to another type of detectable label, such as a fluorescent label. Thus, the level of bound fluorescent antibody can be assessed. Levels of RNA, for example, can also be detected. As alkaline phosphatase is a known enzyme, and the sequences of some genes that encode ALP are available in GENBANK, suitable nucleic acid probes can be designed for use in detection (hybridization) methods of the subject invention. For example, sequence corresponding to 260 amino acids of *Bombyx mori* alkaline phosphatase has been cloned. Thus, for some aspects of this invention (e.g., for some screening methods), various known forms of this protein can be used.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Insect Strains and Brush Border Membrane Vesicle (BBMV) Preparation

*H. virescens* laboratory strains YDK and YHD2 have been previously described [18]. YDK is the unselected susceptible control colony for the Cry1Ac-selected YHD2 strain, which developed 10,000-fold resistance to Cry1Ac when compared to susceptible YDK larvae [19]. After continuous selection with Cry1Ac, levels of resistance increased to 73,000-fold

[11]. Fifth instar larvae from each strain were dissected and midguts frozen and kept at −80° C. until used to prepare BBMV.

BBMV were isolated by the differential centrifugation method of Wolfersberger et al. [20]. BBMV proteins were quantified by the method of Bradford [21], using BSA as standard, and kept at −80° C. until used. N-aminopeptidase (APN) activity using leucine-p-nitroanilide as the substrate was used as a marker for brush border enzyme enrichment in the BBMV preparations. APN activities were enriched 6-8 fold in the BBMV preparations compared to initial midgut homogenates.

Example 2

Cry1Ac Toxin Purification and Labeling

*B. thuringiensis* strain HD-73 obtained from the *Bacillus* Genetic Stock Center (Ohio, USA) was used to produce Cry1Ac. Mutated Cry1Ac $^{509}QNR^{511}$-509AAA$^{511}$ was expressed in *Escherichia coli* MV 1190 kindly provided by Dr. Donald Dean (Ohio State University, Ohio, USA), and purified as described elsewhere [22]. This Cry 1 Ac mutant toxin lacks the GalNAc binding properties of the wild type toxin [23]. Cry1Ac crystalline inclusions were solubilized, activated and purified as previously described [24]. Purified toxin samples (verified by reducing SDS-10% PAGE) were pooled, protein concentration determined as for BBMV proteins and stored at −80° C. until used.

Purified Cry1Ac (1 µg) was radiolabeled with 0.5 mCi of Na$^{125}$I by the chloramine T method [1]. Specific activities of labeled samples were 3-8 mCi/mg, as determined using the bindability method of Schumacher et al. [25]. Labeled toxins were kept at 4° C. and used within 10 days.

Example 3

Identification of the 68-kDa BBMV Glycoprotein as Alkaline Phosphatase

Figure 1:
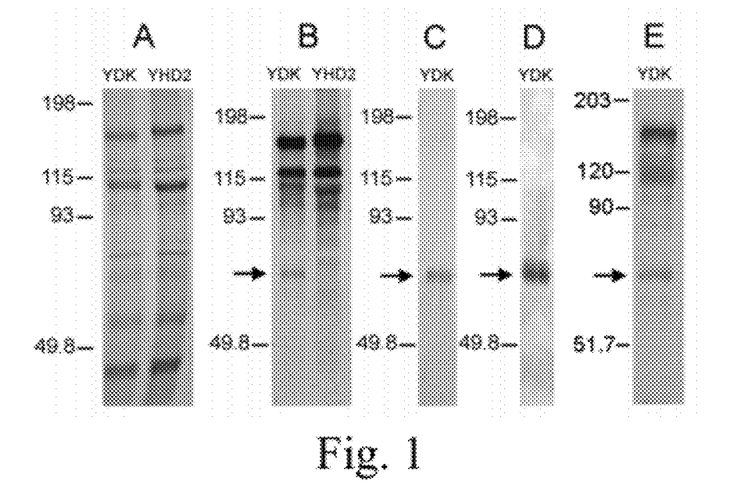
FIG. 1 illustrates identification of the 68 KDa BBMV glycoprotein as HvALP, a form of alkaline phosphatase.

FIG. 1 illustrates identification of the 68-kDa BBMV glycoprotein as HvALP, a form of alkaline phosphatase. BBMV proteins from *H. virescens* strains specified in FIG. 1 were separated by electrophoresis and Coomassie blue stained to control for equal protein loads (FIG. 1A) or transferred to PVDF filters. After blocking, filters were probed with SBA lectin (FIG. 1B) or sera against the membrane bound form of ALP (mALP) from *B. mori* [27]. See FIG. 1C. Blots were developed using enhanced chemiluminescence. Alkaline phosphatase activity in separated BBMV proteins (FIG. 1D) was detected by incubating filters in NBT-BCIP until purple precipitate was visualized in the region of enzymatic activity. For detection of GPI-anchored proteins in BBMV protein blots (FIG. 1E), protein blots were treated with PIPLC and cleaved GPI anchors detected by probing with sera against the CRD determinant. BBMV proteins containing cleaved GPI anchors were visualized by enhanced chemiluminescence. The arrow indicates electrophoretic position of HvALP on the filters.

Although no protein amount differences were detected in Coomassie blue stained gels (FIG. 1A), the 68-kDa protein had reduced soybean agglutinin (SBA) binding in BBMV from YHD2 larvae (FIG. 1B). This protein was recognized by sera against mALP (FIG. 1C) and displayed ALP activity in blots of BBMV proteins (FIG. 1D), demonstrating that this protein is a form of alkaline phosphatase. PIPLC digestion was used to determine whether the 68-kDa protein was GPI anchored to BBMV in *H. virescens*. As shown in FIG. 1E, after PIPLC digestion, anti-CRD sera recognized the 68-kDa protein in *H. virescens* BBMV, suggesting that this protein is GPI-anchored to the brush border membrane. These results also show that the 68-kDa protein with altered glycosylation in the Cry1Ac-resistant YHD2 larvae was a form of ALP. Based on these results, the 68-kDa GPI-anchored glycoprotein was named HvALP for *H. virescens* alkaline phosphatase.

Example 4

Quantification of Alkaline Phosphatase and Aminopeptidase Activities

Specific alkaline phosphatase (ALP) and aminopeptidase-N (APN) enzymatic activities of BBMV proteins were measured using p-nitrophenyl phosphate disodium (pNPP) and leucine-p-nitroanilide (Sigma, St. Louis, Mo., USA) as substrates, respectively. BBMV proteins (1 µg) were mixed with ALP buffer (100 mM Tris/HCl pH 9.5, 100 mM NaCl, 5 mM MgCl$_2$) or PBS buffer (10 mM Na$_2$HPO$_4$ pH 7.5, 135 mM NaCl, 2 mM KCl) containing 1.25 mM pNPP or 0.8 mM leucine-p-nitroanilide, respectively. Enzymatic activities were monitored as changes in OD at 405 nm wavelength for 5 minutes at room temperature (ALP) or at 37° C. (APN) in a microplate reader (Molecular Devices). One enzymatic unit was defined as the amount of enzyme that would hydrolyze 1.0 µmole of substrate to chromogenic product per minute at the specific reaction pH and temperature. Data shown are the mean specific activities from at least four independent BBMV batches from each *H. virescens* strain measured in at least three independent experiments.

Example 5

Importance of Alp Glycosylation for Cry1Ac Binding; Ligand, Lectin and Immunoblots of BBMV Proteins To investigate the oligosaccharides present on HvALP from Cry1Ac susceptible larvae, lectin blotting was performed using selected lectins (Table 1) and BBMV proteins from YDK larvae. After lectin blotting, HvALP on blots was detected by sera against *B. mori* mALP to confirm lectin binding to HvALP.

BBMV proteins (15 or 2 µg) were separated by SDS-PAGE 8%, and gels were either stained or electrotransferred to polyvinylidiene difluoride Q (PVDF) membrane filters (Millipore). After overnight transfer, filters were blocked for one hour at room temperature with PBS buffer containing 0.1% Tween-20 (PBST) and 3% BSA.

For immunoblots, blocked filters were probed with a 1:25, 000 dilution of polyclonal serum against the membrane bound form of alkaline phosphatase (mALP) from *B. mori* (kindly provided by Dr. Masanobu Itoh, Kyoto Institute of Technology, Kyoto, Japan) for one hour. (It should be noted that *B. mori* ALP is one of the few known insect ALPs available, and that these antibodies were not previously used in work in any way associated with studying B.t. proteins.) After washing with PBST containing 0.1% BSA, blots were probed with anti-rabbit serum (Sigma) conjugated to horseradish peroxidase (HRP) or alkaline phosphatase. Filters were developed using enhanced chemiluminescence (ECL, Amersham BioSciences) for peroxidase conjugates, or nitroblue tetrazolium (NBT) and 5-bromo-4-chloro-3-indolyl-phosphate (BCIP) for alkaline phosphatase conjugates. No endogenous alkaline phosphatase activity was detected with NBT-BCIP in blots of BBMV proteins when samples were boiled before electrophoresis. Periodate oxidation treatment of blots prior to immunoblotting did not alter antigenicity of BBMV proteins, showing that the serum used recognized protein and not sugar epitopes.

For lectin blots, blocked filters containing separated BBMV proteins were incubated with lectins from *Canavalia ensiformis* (ConA, at 0.05 µg/ml), *Artocarpus integrifolia* (Jac, at 0.5 µg/ml), *Glycine max* (SBA, at 1 µg/ml), *Ricinus communis* (RCA-I, at 5 µg/ml), *Dolichus biflonus* (DBA, at 5 µg/ml), *Sophora japonica* (SJA, at 5 µg/ml), *Wistaria floribunda* (WFL, at 1 µg/ml), *Helix pomatia* (HPL, at 1 µg/ml), or *Griffonia simplicifolia* (GSL-I, at 5 µg/ml) for one hour in blocking buffer (PBST plus 3% BSA). ConA, Jac, SBA, and HPL were purchased from Sigma; RCA-I, SJA, WFL, and GSL-I were from Vector laboratories (Burlingame, Calif., USA).

Lectins conjugated to HRP were visualized by enhanced chemiluminescence (ECL). Blots of biotinylated lectins were probed with streptavidin-HRP conjugate (Vector) and then visualized as HRP-conjugated lectins. As controls for non-specific lectin binding, lectins were incubated with specific hapten sugars (Table 1) for 30 min. at room temperature before probing BBMV blots. This treatment eliminated or greatly decreased lectin binding to BBMV proteins on filters. See FIG. 2, which illustrates analysis of oligosaccharides on HvALP by lectin blotting. BBMV proteins from YDK larvae were separated by electrophoresis and transferred to PVDF filters. After blocking, filters were probed with specific lectins as indicated in the figure. Lane 1: bound lectins were visualized by enhanced chemiluminescence. Lane 2: immunodetection of HvALP using sera against the mALP from *B. mori*. HvALP was visualized by anti-rabbit-alkaline phosphatase conjugate and NBT-BCIP, so that both lectin blots and HvALP immunodetection could be performed using the same filter. Lane 3: competition of lectin binding with the respective hapten sugar (See Table 1, below). For release of N-linked oligosaccharides from BBMV proteins (PNG-F/SBA), filters were treated with peptide-N-glycanase F (PNG-F). After washing, filters were probed with SBA and developed as for SBA lectin blots. All treatments were replicated at least thrice to confirm reproducibility.

Table 1 shows sugar specificities of lectins (based on [62]) used in blots and respective hapten sugars used for lectin specificity controls. Several lectins were selected according to their specificity of binding to galactose (Gal), N-Acetylgalactosamine (GalNAc), N-Acetylglucosamine (GlcNAc), mannose (Man) or glucose (Glc).

TABLE 1

| Lectin (abbreviation) | Sugar specificity | Hapten sugar |
|---|---|---|
| *Canavalis ensiformis* (ConA) | α-Man<br>α-Glc | 0.2M αmethylman/glc |
| *Artocarpus integrifolia* (Jac) | Galβ1→3GalNAc<br>Galβ1→3,4GlcNAc | 0.8M Gal |
| *Glycine max* (SBA) | α/βGalNAc<br>α/βGal | 0.2M GalNAc |
| *Ricinus communis* (RCA-I) | Galβ1→4GlcNAc<br>Galα1→3Gal | 0.2M Gal |
| *Dolichus biflorus* (DBA) | GalNAcα1→3GalNAc<br>GalNAcα1→3Gal | 0.2M GalNAc |
| *Sophora japonica* (SJA) | Galβ1→3GalNAc<br>Galβ1→3,4GlcNAc | 0.2M Gal |
| *Wistaria floribunda* (WFL) | α/βGalNAc | 0.2M GalNAc |
| *Helix pomatia* (HPL) | GalNAcα1→GalNAc<br>GalNAcα1→3Gal | 0.2M GalNAc |
| *Griffonia simplicifolia* (GSL) | GalNAcα1→3Gal<br>Galα1→3,6Gal/Glc | 0.2M Gal |

For SBA binding competition, filters were blocked as above, and then 12 µg/ml of Cry1Ac or the Cry1Ac mutant protein $^{509}$QNR$^{511}$-$^{509}$AAA$^{511}$ were added to the blocking buffer along with SBA lectin (1 µg/ml). After one-hour incubation and washing, filters were developed as described for lectin blots.

Ligand blots were done as previously described [5]. $^{125}$I-Cry1Ac (1 nM) was used to probe blotted BBMV proteins in blocking buffer for one hour at room temperature. After washing, filters were exposed to photographic film at −80° C. for 24 hours.

To detect HvALP in the filters used for lectin or ligand blotting, after development, filters were washed in PBST plus 0.1% BSA overnight. Blocking and HvALP immunodetection were performed as described above. To avoid interference with lectin or toxin detection, bound mALP antisera was detected by anti-rabbit sera conjugated to alkaline phosphatase.

Figure 2:
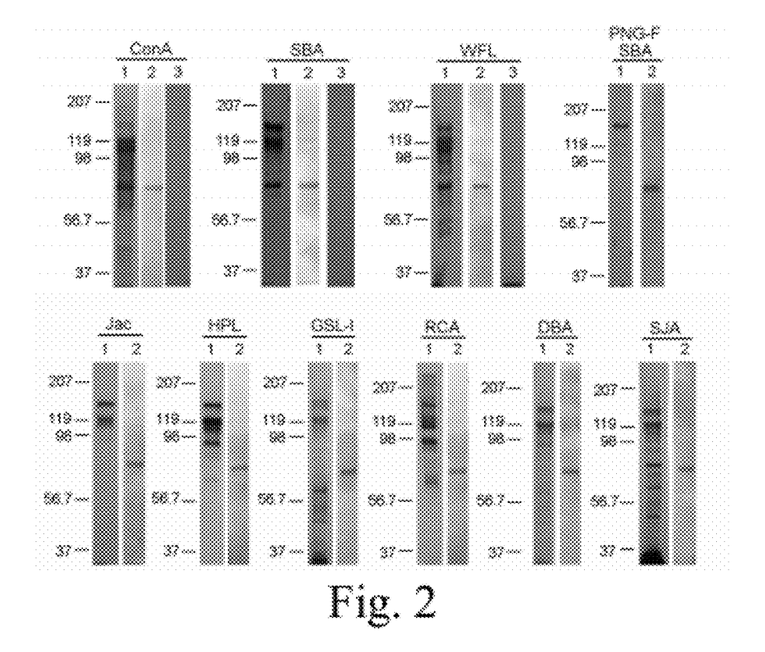

As shown in FIG. 2, HvALP was recognized by lectins from *Canavalia ensiformis* (ConA), *Glycine max* (SBA), and *Wistaria floribunda* (WFL). The different pattern of BBMV proteins being recognized by both SBA and WFL (both bind terminal GalNAc) was probably due to the existence of terminal GalNAc in linkages poorly recognized by one of the lectins. Conversely, no binding to HvALP was detected using lectins from *Artocarpus integrifolia* (Jac), *Ricinus communis* (RCA), *Dolichus biflorus* (DBA), or *Helix pomatia* (HPL). Although proteins of similar size to HvALP were bound by *Griffonia simplicifolia* (GSL) and *Sophora japonica* (SJA) lectins, immunodetection of HvALP in these filters demonstrated that the detected lectin binding proteins were not HvALP. To further test the existence of terminal GalNAc on N-linked oligosaccharides on HvALP, we performed digestion of blotted BBMV proteins with peptide-N-glycosidase-F (PNG-F), which releases N-linked oligosaccharides as N-glycosides from polypeptide chains. Digestion of BBMV proteins with PNG-F eliminated binding of SBA to HvALP (FIG. 2), supporting the hypothesis that this protein has N-linked oligosaccharides with terminal GalNAc residues. Binding of SBA to other BBMV proteins was also decreased after PNG-F digestion, suggesting the presence of GalNAc or galactose on N-linked oligosaccharides in these proteins. Thus, according to one aspect of the subject invention, an insect (or insects) can also be screened for the presence or absence (or reduced amounts) of glycosylation to determine if the insect is resistant to crystal protein toxins (which would be indicated by decreased amounts of bound lectins (preferably SBA).

Example 6

Digestion of BBMV Proteins with Peptide-N-Glycosidase F

Release of N-linked oligosaccharides from BBMV proteins was achieved by digestion of blotted BBMV proteins with peptide-N-glycosidase F (PNG-F). BBMV proteins (15 µg) were separated by SDS-8% PAGE and transferred to PVDF filters as above. Filters were incubated in 5 ml of PBS buffer (pH 7.4) containing 0.1% SDS, 0.5% Triton-X-100 and 30 units of PNG-F (Boehringer-Mannheim) for 17 hours at 37° C. After treatment, filters were blocked and probed as for SBA lectin blots or $^{125}$I-Cry1Ac ligand blots. Controls, which had no PNG-F in the incubation buffer, showed no differences in lectin or toxin binding when compared to SBA and $^{125}$I-Cry1Ac blots.

Example 7

Detection of GPI Anchors

The presence of glycosylphosphatidylinositol (GPI) anchors in BBMV proteins was detected following the method described by Luo et al. [8]. Briefly, after phosphatidylinositol-specific phospholipase C (PIPLC) digestion of BBMV blots, cleaved GPI anchors were detected by immunological detection of the exposed cross-reacting determinant (CRD) epitope contained in the residue of the GPI anchor by probing with anti-CRD sera (kindly provided by Dr. Mensa-Wilmot, University of Georgia, Athens, Ga., USA). Blots were probed with anti-rabbit-HRP conjugate (Sigma) before developing with enhanced chemiluminescence as above. In controls, which had no PIPLC in the blocking buffer, no proteins were detected.

Example 8

Detection of Alkaline Phosphatase Activity in SDS-PAGE Gels and Blots

To detect alkaline phosphatase activity in BBMV, proteins (15 or 2 µg) solubilized in sample buffer [26] were not heat denatured before gel loading. After SDS-PAGE 8% electrophoresis and transfer to PVDF, filters were washed with ALP buffer for 15 minutes at room temperature. After addition of 330 µg/ml of NBT and 165 µg/ml of BCIP to the ALP buffer, alkaline phosphatase activity was visualized by the formation of a purple-red precipitate. Reactions were stopped by incubation of filters in 50 ml of PBS pH 7.5 containing 200 µl of 500 mM EDTA pH 8.0.

Example 9

Importance of ALP Glycosylation for Cry1Ac Binding

To test the hypothesis that Cry1Ac toxin bound to the terminal GalNAc residue on HvALP, SBA binding to HvALP was competed with Cry1Ac. The reciprocal competition assay was not performed due to the $10^6$-fold lower affinity of SBA for GalNAc ($K_d$=0.3 mM; [28]) when compared to Cry1Ac affinity for its binding sites ($K_d$=1.1 nM; [5]).

Figure 3:
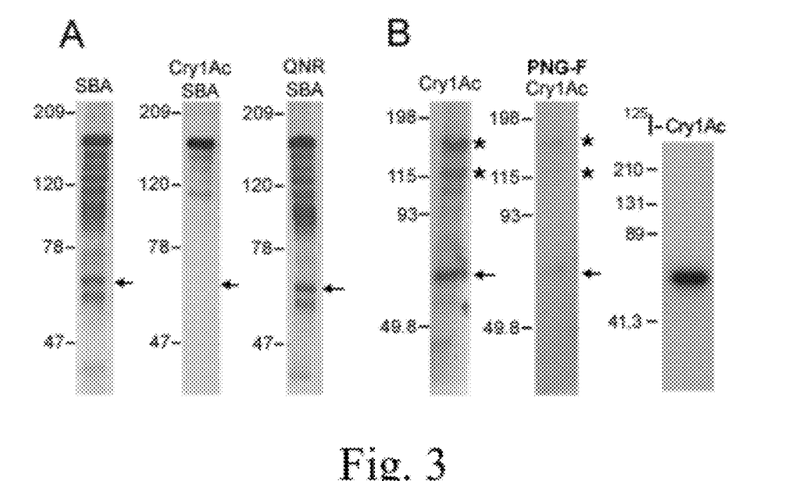
FIG. 3 shows investigation of Cry1Ac binding to N=linked oligosaccharides on HvALP. First three panels of FIG. 3 are 3A, 3B, 3C respectively; the last three panels of FIGS. 3 and 3D, FIG. 3A: SBA binds to HvALP protein as well as other BBMV proteins such as 170 KDa APN normally.

FIG. 3 shows investigation of Cry1Ac binding to N-linked oligosaccharides on HvALP. For competition of SBA binding (A), blocked PVDF filters containing separated BBMV proteins from YDK larvae were probed with SBA lectin (SBA) or SBA lectin plus either Cry1Ac (Cry1Ac/SBA) or the Cry1Ac mutant $^{509}$QNR$^{511}$-$^{509}$AAA$^{511}$ (QNR/SBA), which lacks GalNAc binding. Bound SBA lectin was detected by enhanced chemiluminescence. For ligand blots (B), BBMV proteins binding Cry1Ac were detected by probing blocked filters with 1 nM $^{125}$I-Cry1Ac for one hour (Cry1Ac). Importance of N-linked oligosaccharides for $^{125}$I-Cry1Ac binding (PNG/Cry1Ac) was tested by digestion of BBMV proteins with PNG-F glycosidase. After digestion, filters were washed, blocked and treated as described for ligand blots. Bound toxin was detected by autoradiography. Asterisks indicate the electrophoretic position of the 170- and 130-kDa proteins, arrows indicate the position of HvALP in the filters. Radiography of the radiolabeled Cry1Ac toxin used for these experiments ($^{125}$I-Cry1Ac) is included.

When comparing SBA binding to BBMV (FIG. 3A) with Cry1Ac competition blots (FIG. 3B), Cry1Ac prevented SBA binding to HvALP as well as to other BBMV proteins, indicative of toxin binding to terminal GalNAc residues on these proteins. Binding of SBA to the 170-kDa APN was almost unaffected by the presence of Cry1Ac. As a control for toxin binding not due to GalNAc recognition, we competed SBA binding with a Cry1Ac mutant, $^{509}$QNR$^{511}$-$^{509}$AAA$^{511}$, which lacks GalNAc binding [23]. SBA binding to HvALP was unchanged by $^{509}$QNR$^{511}$-$^{509}$AAA$^{511}$ (FIG. 3C), demonstrating that Cry1Ac bound to terminal GalNAc on HvALP.

To provide further support for the hypothesis of Cry1Ac binding to GalNAc on HvALP, ligand blots were performed with $^{125}$I-Cry1Ac. Cry1Ac bound to several BBMV proteins, including HvALP (FIG. 3D). When N-linked oligosaccharides were released from HvALP by PNG-F digestion, Cry1Ac did not bind to this protein, demonstrating that toxin binding was dependent on the presence of N-linked oligosaccharides on HvALP. Binding to other Cry1Ac binding proteins was also greatly decreased by PNG-F digestion, indicating the importance of N-linked protein glycosylation for Cry1Ac binding on blots.

Example 10

Reduced HvALP Correlates with Resistance to Cry1Ac

To investigate the possibility that reduced SBA binding to HvALP from YHD2 larvae (FIG. 1B) was a result of decreased HvALP protein levels, the following comparisons were conducted using immunodetection and alkaline phosphatase activity blots: HvALP from YHD2, YDK, and larvae from the F1 generation of backcrosses between YDK and YHD2 adults. Two different types of F1 larvae, according to the sex of the susceptible parent, were used to determine the potential existence of sex linkage. As shown in FIG. 4B, sera against the membrane-bound form of alkaline phosphatase from *B. mori* recognized HvALP in BBMV from YDK, YHD2 and F1 larvae. No differences in intensity of recognition were observed between HvALP from YDK and F1 vesicles, while recognition of HvALP in YHD2 was clearly reduced.

Figure 4:
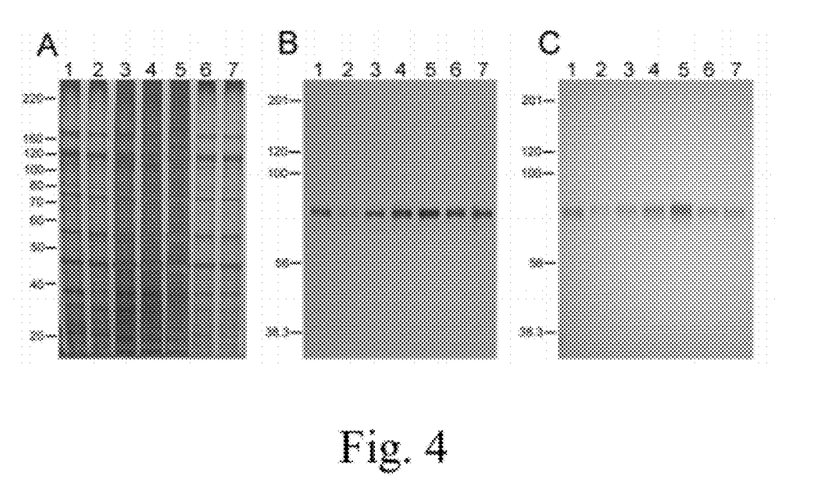
FIG. 4 illustrates a comparison of HvALP levels and alkaline phosphatase activity between BBMV from susceptible and resistant *H. virescens* larvae. Lanes 3-5 contain YHD2 proteins 3, 5, 10-fold respectively the protein concentration used for YDK (lane 1) and F1 cross of YDK and YHD2 (lanes 6 and 7).
Figure 5:
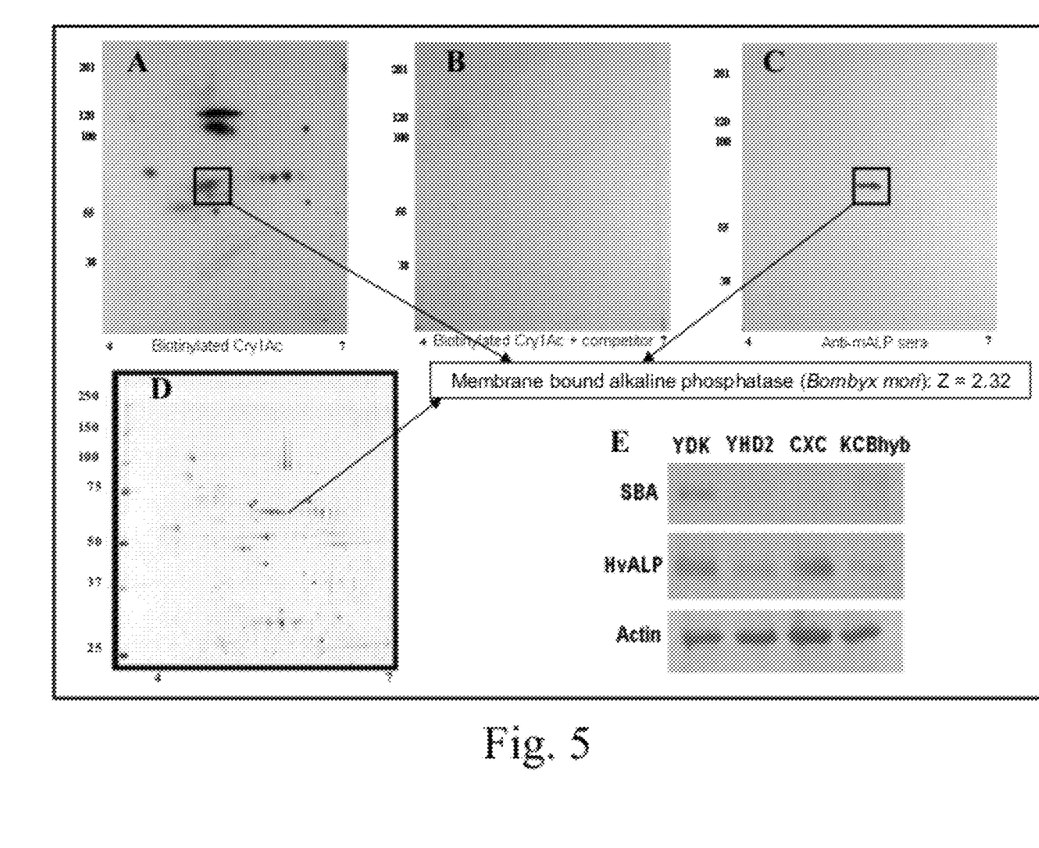
FIG. 5 shows Cry1Ac ligand blot (A and B), HvALP immunodetection (C) and identification of HvALP protein spots from a 2D gel (D) by PMF searches. E shows detection of HvALP by soybean agglutinin (SBA) or sera against mALP (HvALP) in BBMV from different H. VIRESECENS strains.

FIG. 4 illustrates a comparison of HvALP levels and alkaline phosphatase activity between BBMV from susceptible and resistant *H. virescens* larvae. BBMV proteins from YDK (lane 1), YHD2 (lane 2), F1 generation of YDK males crossed with YHD2 females (lane 6), or F1 generation of YDK females crossed with YHD2 males (lane 7), were separated by electrophoresis. For comparison, lanes 3, 4 and 5 contained YHD2 BBMV proteins at 3-, 5-, and 10-fold respectively the protein concentration used for YDK and F1 lanes. Gels were Coomassie blue stained (panel A), or transferred to PVDF filters (panels B and C). After blocking, blot in panel B was probed with sera against the mALP from *B. mori* to detect HvALP. For visualization of alkaline phosphatase activity (panel C), the filter was washed in ALP buffer, and then NBT-BCIP included in the buffer as described in Materials and Methods. Alkaline phosphatase activity was visualized as a purple precipitate.

To confirm reduction in HvALP antigen in BBMV from YHD2, the protein load was increased by 3-, 5- and 10-fold to compare to YDK and F1 vesicles. Increased BBMV protein concentrations as observed in the stained gel (FIG. 4A) resulted in augmented HvALP recognition (lanes 3, 4 and 5 in FIG. 4B), clearly suggesting a reduction in HvALP protein levels in BBMV from YHD2 larvae. Visual comparison of the lanes with increasing YHD2 protein loads and the YDK and F1 lanes in the blots (FIG. 4B) suggested a 3- to 5-fold reduction in HvALP antigen levels in BBMV from YHD2 larvae when compared to YDK or F1 vesicle proteins.

Thus, it was predicted that reduced HvALP amounts in BBMV from YHD2 larvae would result in reduced alkaline phosphatase activity. Alkaline phosphatase activity in blots of BBMV proteins from YDK and F1 larvae was similar, and higher than activity in YHD2 vesicles (FIG. 4C). In agreement with reduced protein levels observed in FIG. 4B, specific alkaline phosphatase activity in suspensions of BBMV from YHD2 insects was reduced 3- to 4-fold when compared to YDK or F1 vesicles (see Table 2, below). Aminopeptidase-N specific activity was used as control, with no significant differences found between BBMV from YDK, YHD2 or F1 larvae.

Table 2 shows specific alkaline phosphatase (ALP) and aminopeptidase-N (APN) activities of BBMV suspensions from YDK, YHD2 and F1 larvae. Specific activity of BBMV suspensions is expressed in units per milligram of BBMV protein (U/mg). One enzymatic unit was defined as the amount of enzyme that would hydrolyze 1.0 μmole of substrate to chromogenic product per minute at the specific reaction pH and temperature. SD=standard deviation of the mean based on at least six independent measurements.

TABLE 2

| BBMV sample | ALP activity (U/mg) ± SD | APN activity (U/mg) ± SD |
|---|---|---|
| YDK | 223 ± 91 | 2192 ± 427 |
| YHD2 | 77 ± 37 | 2364 ± 290 |
| YDK♀ × YHD2♂ | 375 ± 12 | 3156 ± 62 |
| YHD2♀ × YDK♂ | 292 ± 12 | 2921 ± 275 |

These results indicated that reduced amounts of HvALP in BBMV from YHD2 larvae result in reduced alkaline phosphatase activity and correlate with resistance to Cry1Ac and reduced Cry1Ac toxin binding.

Example 11

Further Characterization of the Nature of HvALP as a Cry1Ac Receptor and Alteration of this Receptor in Resistant YHD2 Larvae Two main approaches are discussed in this Example: (1) proteomic analysis through 2D in-gel differential electrophoresis (2D-DIGE) of susceptible and resistant BBMV proteins to identify changes related to HvALP, and (2) studies on the molecular mechanism responsible for reduced HvALP levels in resistant larvae. Towards completion of (1), Peptide Mass Fingerprints (PMFs) of BBMV protein spots were identified as HvALP based on detection by sera against the mALP from *Bombyx mori* (FIG. 2C) and specific Cry1Ac binding on 2D ligand blots (FIGS. 2A and 2B). Database searches using the obtained PMFs identified the protein spots as membrane bound alkaline phosphatase. These results also highlight the utility of PMF database searches to identify proteins separated in 2D gels and identify HvALP as a Cry1Ac binding protein in 2D ligand blots.

Relative to (2), in further studying HvALP alteration as a mechanism for Cry1Ac resistance, HvALP in susceptible (YDK) and additional resistant *H. virescens* strains (CXC, and KCBhyb) was compared using SBA lectin blots, immunoblots with anti-mALP sera, and measurements of ALP activity in BBMV.

FIG. 5 shows Cry1Ac ligand blots (A and B), HvALP immunodetection (C), and identification of HvALP protein spots from a 2D gel (D) by PMF searches. BBMV proteins from susceptible larvae were separated by 2D electrophoresis, then stained with Sypro Ruby stain (D) or transferred to PVDF filters. After blocking, filters were probed with 5 nM biotinylated Cry1Ac (A) and 500-fold excess unlabeled Cry1Ac as competitor (B) or with sera against the mALP from *B. mori* (C). Protein spots from (D) were digested with trypsin and the resulting PMFs were used for database searches. Identification of the spots is indicated. The Z value is a measure of probability (values higher than 2.3 denote 95% confidence of correct match). (E) Detection of HvALP by soybean agglutinin (SBA) or sera against mALP (HvALP) in BBMV from different *H. virescens* strains. Immunodetection of actin in the same samples was used as loading control.

As shown in FIG. 5E, HvALP levels were reduced in BBMV from YHD2 and KCBhyb larvae when compared to YDK and CXC vesicles. SBA binding, which reflects the presence of terminal GalNAc residues recognized by Cry1Ac (EJB manuscript), was greatly reduced in BBMV from all the resistant strains.

Alkaline phosphatase (ALP) and aminopeptidase-N (APN) activities in BBMV from susceptible (YDK) and resistant (YHD2, CXC, KCBHyb) strains of *H. virescens* were assayed. In agreement with the HvALP alterations, ALP activity was reduced in BBMV from YHD2 (129±65 U/mg), CXC (116±65 U/mg), and KCBhyb (123±67 U/mg) when compared to YDK (362±135 U/mg) vesicles. Assays were performed as described in Jurat-Fuentes and Adang (2004). Specific activity (±standard deviation) is expressed in units per milligram of BBMV protein (U/mg). One unit is defined as the amount of enzyme that will hydrolyze 1.0 μmole of p-nitrophenyl phosphate (PNPP) to p-nitrophenol (PNP) and phosphate per minute at pH 9.5 at 25° C.

Therefore, these results suggest that alterations of (including reductions in the amount of) HvALP (in protein amounts, activities, and/or glycosylation) correlate with resistance to Cry1Ac, and those HvALP alterations may be used as resistance markers.

REFERENCES

1. Garczynski, S. F., Crim, J. W. & Adang, M. J. (1991) Identification of putative insect brush border membrane-binding molecules specific to *Bacillus thuringiensis* delta-endotoxin by protein blot analysis, *Appl. Environ. Microbiol.* 57, 2816-2820.
2. Van Rie, J., Jansens, S., Hofte, H., Degheele, D. & Van Mellaert, H. (1990) Receptors on the brush border membrane of the insect midgut as determinants of the specificity of *Bacillus thuringiensis* delta-endotoxins, *Appl. Environ. Microbiol.* 56, 1378-1385.
3. Hofmann, C., Vanderbruggen, H., Heofte, H., Van Rie, J., Jansens, S. & Van Mellaert, H. (1988) Specificity of *Bacillus thuringiensis* delta-endotoxins is correlated with the presence of high-affinity binding sites in the brush border membrane of target insect midguts, *Proceedings of the National Academy of Sciences of the United States of America.* 85(21), 7844-8.

4. Whalon, M. E. & Wingerd, B. A. (2003) Bt: Mode of action and use, *Arch. Insect Biochem. Physiol.* 54, 200-211.
5. Jurat-Fuentes, J. L. & Adang, M. J. (2001) Importance of Cry1 delta-endotoxin domain II loops for binding specificity in *Heliothis virescens* (L.), *Appl. Environ. Microbiol.* 67, 323-329.
6. Van Rie, J., Jansens, S., Heofte, H., Degheele, D., Van Mellaert, H. & Plant Genetic Systems, G. B. (1989) Specificity of *Bacillus thuringiensis* delta-endotoxins. Importance of specific receptors on the brush border membrane of the mid-gut of target insects, *European journal of biochemistry/FEBS.* 186(1-2), 239-47.
7. Banks, D. J., Jurat-Fuentes, J. L., Dean, D. H. & Adang, M. J. (2001) *Bacillus thuringiensis* Cry1Ac and Cry1Fa delta-endotoxin binding to a novel 110 kDa aminopeptidase in *Heliothis virescens* is not N-acetylgalactosamine mediated, *Insect Biochem. Molec. Biol.* 31, 909-918.
8. Luo, K., Sangadala, S., Masson, L., Mazza, A., Brousseau, R. & Adang, M. J. (1997) The *Heliothis virescens* 170 kDa aminopeptidase functions as "receptor A" by mediating specific *Bacillus thuringiensis* Cry1A delta-endotoxin binding and pore formation, *Insect Biochem. Molec. Biol.* 27, 735-743.
9. Oltean, D. I., Pullikuth, A. K., Lee, H. K. & Gill, S. S. (1999) Partial purification and characterization of *Bacillus thuringiensis* Cry1A toxin receptor A from *Heliothis virescens* and cloning of the corresponding cDNA, *Appl. Environ. Microbiol.* 65, 4760-4766.
10. Gahan, L. J., Gould, F. & Heckel, D. G. (2001) Identification of a gene associated with Bt resistance in *Heliothis virescens, Science.* 293, 857-860.
11. Jurat-Fuentes, J. L., Gould, F. L. & Adang, M. J. (2002) Altered Glycosylation of 63- and 68-kilodalton microvillar proteins in *Heliothis virescens* correlates with reduced Cry1 toxin binding, decreased pore formation, and increased resistance to *Bacillus thuringiensis* Cry1 toxins, *Appl. Environ. Microbiol.* 68, 5711-5717.
12. Mohammed, S. I., Johnson, D. E., Aronson, A. I. & Department of Biological Sciences, P. U. W. L. I. U.S.A. (1996) Altered binding of the Cry1Ac toxin to larval membranes but not to the toxin-binding protein in *Plodia interpunctella* selected for resistance to different *Bacillus thuringiensis* isolates, *Applied and environmental microbiology.* 62(11), 4168-73.
13. McNall, R. J. & Adang, M. J. (2003) Identification of novel *Bacillus thuringiensis* Cry1Ac binding proteins in *Manduca sexta* midgut through proteomic analysis, *Insect Biochem. Molec. Biol.* 33, 999-1010.
14. Takesue, Y., Yokota, K., Miyajima, K., Taguchi, R. & Ikezawa, H. (1989) Membrane anchors of alkaline phosphatase and trehalase associated with the plasma membrane of larval midgut epithelial cells of the silkworm, *Bombyx mori, J. Biochem.* 105, 998-1001.
15. Ikezawa, H., Yamanegi, M., Taguchi, R., Miyashita, T. & Ohyabu, T. (1976) Studies on Phosphatidylinositol Phosphodiesterase (Phospholipase-C Type) of *Bacillus*-Cereus .1. Purification, Properties and Phosphatase-Releasing Activity, *Biochimica Et Biophysica Acta.* 450, 154-164.
16. Sangadala, S., Walters, F. S., English, L. H. & Adang, M. J. (1994) A mixture of *Manduca sexta* aminopeptidase and phosphatase enhances *Bacillus thuringiensis* insecticidal CryIA(c) toxin binding and $^{86}Rb^{(+)}$-$K^+$ efflux in vitro, *J. Biol. Chem.* 269, 10088-10092.
17. English, L. & Readdy, T. L. (1989) Delta endotoxin inhibits a phosphatase in midgut epithelial membranes of *Heliothis virescens, Insect Biochem.* 19, 145-152.
18. Gould, F., Anderson, A., Reynolds, A., Bumgarner, L. & Moar, W. (1995) Selection and genetic analysis of a *Heliothis virescens* (Lepidoptera: noctuidae) strain with high levels of resistance to *Bacillus thuringiensis* toxins, *J. Econ. Entomol.* 88, 1545-1559.
19. Lee, M. K., Rajamohan, F., Gould, F. & Dean, D. H. (1995) Resistance to *Bacillus thuringiensis* CryIA δ-endotoxins in a laboratory-selected *Heliothis virescens* strain is related to receptor alteration, *Appl. Environ. Microbiol.* 61, 3836-3842.
20. Wolfersberger, M. G., Luthy, P., Maurer, A., Parenti, P., Sacchi, V. F., Giordana, B. & Hanozet, G. M. (1987) Preparation and partial characterization of amino acid transporting brush border membrane vesicles from the larval midgut of the cabbage butterfly (*Pieris brassicae*), *Comp. Biochem. Physiol.* 86A, 301-308.
21. Bradford, M. (1976) A rapid and sensitive method for the quantitation of microgram quantities of protein utilizing the principle of protein-dye binding, *Anal. Biochem.* 72, 248-254.
22. Lee, M. K., Milne, R. E., Ge, A. Z., Dean, D. H. & Department of Biochemistry, O. S. U. C. (1992) Location of a *Bombyx mori* receptor binding region on a *Bacillus thuringiensis* delta-endotoxin, *The Journal of biological chemistry.* 267(5), 3115-21.
23. Lee, M. K., You, T. H., Gould, F. L., Dean, D. H. & Department of Biochemistry, T. O. S. U. C. O. U.S.A. (1999) Identification of residues in domain III of *Bacillus thuringiensis* Cry1Ac toxin that affect binding and toxicity, *Applied and environmental microbiology.* 65(10), 4513-20.
24. Luo, K., Banks, D. & Adang, M. J. (1999) Toxicity, binding and permeability analyses of four *Bacillus thuringiensis* Cry1 δ-endotoxins by use of brush border membrane vesicles of *Spodoptera exigua* and *Spodoptera frugiperda, Appl. Environ. Microbiol.* 65, 457-464.
25. Schumacher, C. & von Tscharner, V. (1994) Practical instructions for radioactively labeled ligand receptor binding studies, *Anal. Biochem.* 222, 262-269.
26. Laemmli, U. K. (1970) Cleavage of structural proteins during the assembly of the head of bacteriophage T4, *Nature.* 227, 680-685.
27. Azuma, M. & Eguchi, M. (1989) Discrete localization of distinct alkaline phosphatase isozymes in the cell surface of silkworm midgut epithelium, *J. Exp. Zool.* 251, 108-112.
28. De Boeck, H., Lis, H., van Tilbeurgh, H., Sharon, N. & Loontien, F. G. (1984) Binding of simple carbohydrate and some of their chromophoric derivatives to soybean agglutinin as followed by ttrimetric procedures and stopped flow kinetics, *J. Biol. Chem.* 259, 7067-7074.
29. Eguchi, M. (1995) Alkaline phosphatase isozymes in insects and comparison with mammalian enzyme, *Comp. Biochem. Physiol.* 111B, 151-162.
30. Cerneus, D., Ueffing, E., Posthuma, G., Strous, G. & van der Ende, A. (1993) Detergent insolubility of alkaline phosphatase during biosynthetic transport and endocytosis. Role of cholesterol, *J. Biol. Chem.* 268, 3150-3155.
31. Zhuang, M., Oltean, D. I., Gomez, I., Pullikuth, A. K., Soberon, M., Bravo, A. & Gill, S. S. (2002) *Heliothis virescens* and *Manduca sexta* lipid rafts are involved in Cry1A toxin binding to the midgut epithelium and subsequent pore formation, *J. Biol. Chem.* 277, 13863-13872.
32. Yamamoto, H., Azuma, M. & Eguchi, M. (1991) further characterization of alkaline phosphatase isozymes in the islkworm midgut: Effects of amino acids and metal ions and comparison of sugar chains, Comp. Biochem. Physiol. 99B, 437-443.

33. Debray, H., Decout, D., Strecker, G., Spik, G. & Montreuil, J. (1981) Specificity of twelve lectins towards oligosaccharides and peptides related to N-glycosylproteins, *Eur. J. Biochem.* 117, 41-55.
34. Van den Steen, P., Rudd, P. M., DWEK, R. A. & Opdenakker, G. (1998) Concepts and principles of O-linked glycosylation, *Critical Reviews In Biochemistry And Molecular Biology.* 33, 151-208.
35. Wilson, I. B. H. (2002) Glycosylation of proteins in plants and invertebrates, *Current Opinion in Structural Biology.* 12, 569-577.
36. Samuel J. E., L. P. P., S. Ward, A. D. O'Brien, V. Ginsburg, and H. C. Krivan. (1990) Comparison of the glycolipid receptor specificities of Shiga-like toxin type II and Shiga-like toxin type II variants., *Infect. Immun.* 58, 611-618.
37. Menezes, C. A., Amianti, J., Harayama, H. S., Koga, P. C. M., Trabulsi, L. R. & Piazza, R. M. F. (2002) Inhibition of *Escherichia coli* heat-labile enterotoxin by neoglycoprotein and anti-lectin antibodies which mimic GM1 receptor, *FEMS Microbiology Letters.* 216, 67-70.
38. Burton, S. L., Ellar, D. J., Li, J. & Derbyshire, D. J. (1999) N-acetylgalactosamine on the putative insect receptor aminopeptidase N is recognised by a site on the domain III lectin-like fold of a *Bacillus thuringiensis* insecticidal toxin, *J. Mol. Biol.* 287, 1011-1022.
39. Sangadala, S., Azadi, P., Carlson, R., Adang, M. J. & Department of Entomology, U. o. G. A. G. A. U.S.A. (2001) Carbohydrate analyses of *Manduca sexta* aminopeptidase N, co-purifying neutral lipids and their functional interactions with *Bacillus thuringiensis* Cry1Ac toxin, *Insect biochemistry and molecular biology.* 32(1), 97-107.
40. Knowles, B. H., Knight, P. J., Ellar, D. J. & Department of Zoology, U. o. C. U. K. (1991) N-acetyl galactosamine is part of the receptor in insect gut epithelia that recognizes an insecticidal protein from *Bacillus thuringiensis, Proceedings of the Royal Society of London. Series B. Biological sciences.* 245(1312), 31-5.
41. Derbyshire, D. J., Ellar, D. J. & Li, J. (2001) Crystallization of the *Bacillus thuringiensis* toxin Cry1Ac and its complex with the receptor ligand N-acetyl-D-galactosamine, *Acta Crystallogr. D Biol. Crystallogr.* 57, 1938-1944.
42. Kang, S., Cummings, R. D. & McCall, J. W. (1993) Characterization of the N-linked oligosaccharides in glycoproteins synthesized by microfilariae of *Dirofilaria immitis., J. Parasitol.* 79, 815-828.
43. Wilkins, S. & Billingsley, P. F. (2001) Partial characterization of oligosaccharides expressed on midgut microvillar proteins of the mosquito, *Anopheles stephensi* Liston, *Insect Biochem. Molec. Biol.* 31, 937-948.
44. Van Die, I., A. van Tetering, H. Bakker, D. H. van den Eijnden, and D. H. Joziasse. (1996) Glycosylation in lepidopteran insect cells: identification of a β1,4-N-Acetylgalactosaminyltransferase involved in the synthesis of complex-type oligosaccharide chains., *Glycobiology.* 6, 157-164.
45. Kuik, J. A. V., Sijbesma, R. P., Kamerling, J. P., Vliegenthart, J. F. & Wood, E. J. (1987) Primary structure determination of seven novel N-linked carbohydrate chains derived from hemocyanin of *Lymnaea stagnalis*. 3-O-methyl-D-galactose and N-acetyl-D-galactosamine as constituents of xylose-containing N-linked oligosaccharides in an animal glycoprotein., *Eur. J. Biochem.* 169, 399-411.
46. Sato, T., K. Furukawa, D. E. Greenwalt, and A. Kobata. (1993) Most bovine milk fat globule membrane glycoproteins contain asparagine-linked sugar chains with GalNAcβ1,4GlcNAc groups., *J. Biochem.* 114, 890-900.
47. Nyame, K., Smith, D., Damian, R. & Cummings, R. (1989) Complex-type asparagine-linked oligosaccharides in glycoproteins synthesized by *Schistosoma mansoni* adult males contain terminal beta-linked N-acetylgalactosamine, *J. Biol. Chem.* 264, 3235-3243.
48. Kubelka, V., Altmann, F. & Marz, L. (1995) The asparagine-linked carbohydrate of honeybee venom hyaluronidase, *Glycoconjugate Journal.* 12, 77-83.
49. Cundell, D. R. & Tuomanen, E. I. (1994) Receptor specificity of adherence of *Streptococcus pneumoniae* to human type-II pneumocytes and vascular endothelial cells in vitro, *Microbial Pathogenesis.* 17, 361-374.
50. Wenneras, C., Neeser, J. & Svennerholm, A. (1995) Binding of the fibrillar CS3 adhesin of enterotoxigenic *Escherichia coli* to rabbit intestinal glycoproteins is competitively prevented by GalNAc beta 1-4Gal-containing glycoconjugates, *Infect. Immun.* 63, 640-646.
51. Nelson, K. L. & Buckley, J. T. (2000) Channel Formation by the Glycosylphosphatidylinositol-anchored Protein Binding Toxin Aerolysin Is Not Promoted by Lipid Rafts, *J. Biol. Chem.* 275, 19839-19843.
52. Fukushima, K., Ikehara, Y., Kanai, M., Kochibe, N., Kuroki, M. & Yamashita, K. (2003) A {beta}-N-Acetylglucosaminyl Phosphate Diester Residue Is Attached to the Glycosylphosphatidylinositol Anchor of Human Placental Alkaline Phosphatase: a target of the channel-forming toxin aerolysin, *J. Biol. Chem.* 278, 36296-36303.
53. Griffitts, J. S., Huffman, D. L., Whitacre, J. L., Barrows, B. D., Marroquin, L. D., Muller, R., Brown, J. R., Hennet, T., Esko, J. D. & Aroian, R. V. (2003) Resistance to a bacterial toxin is mediated by removal of a conserved glycosylation pathway required for toxin-host interactions, *J. Biol. Chem.* 278, 45594-45602.
54. Beckman, L. & Johnson, F. M. (1964) Variations in larval alkaline phosphatase controlled by Aph alleles in *Drosophila melanogaster, Genetics.* 49, 829-835.
55. Igbokwe, E. C. & Mills, M. (1982) Electrophoretic variability in the phosphatase system of the yellow-fever mosquito, *Aedes aegypti, Comp. Biochem. Physiol.* 73B, 457-458.
56. Takeda, S., Azuma, M., Itoh, M. & Eguchi, M. (1993) The Strain Difference and Analysis of Polymorphic Nature of Membrane-Bound Alkaline-Phosphatase in the Midgut Epithelium of the Silkworm, *Bombyx-Mori, Comparative Biochemistry and Physiology B-Biochemistry & Molecular Biology.* 104, 81-89.
57. Itoh, M., Kanamori, Y., Takao, M. & Eguchi, M. (1999) Cloning of soluble alkaline phosphatase cDNA and molecular basis of the polymorphic nature in alkaline phosphatase isozymes of *Bombyx mori* midgut, *Insect Biochem. Molec. Biol.* 29, 121-129.
58. Tabashnik, B. E., Carriere, Y., Dennehy, T. J., Morin, S., Sisterson, M. S., Roush, R. T., Shelton, A. M. & Zhao, J.-Z. (2003) Insect Resistance to Transgenic Bt Crops: Lessons from the Laboratory and Field, *Journal of Economic Entomology.* 96, 1031-1038.
59. Chang, W., Zachow, K. & Bentley, D. (1993) Expression of epithelial alkaline phosphatase in segmentally iterated bands during grasshopper limb morphogenesis, *Development.* 118, 651-663.
60. Lu, Y. J. & Adang, M. J. (1996) Conversion of *Bacillus thuringiensis* CryIAc-binding aminopeptidase to a soluble form by endogenous phosphatidylinositol phospholipase C, *Insect Biochem. Molec. Biol.* 226, 33-40.

61. Eguchi, M., Sawaki, M. & Suzuki, Y. (1972) Multiple forms of midgut alkaline phosphatase in the silkworm: new band formation and the relationship between the midgut and digestive fluid enzymes, *Insect Biochemistry.* 2, 297-304.

62. Wu, A. M., Song, S. C., Sugii, S. & Herp, A. (1997) Differential binding properties of Gal/GalNAc specific lectins available for characterization of glycoreceptors, *Indian J. Biochem. Biophys.* 34, 61-71.

The invention claimed is:

1. A method of screening a lepidopteran for resistance to a *Bacillus thuringiensis* (B.t) insecticidal Cry1 protein that is toxic to lepidopterans, wherein said lepdopteran is of a species known to develop resistance to said Cry1 protein, wherein said method comprises collecting a lepidopteran from a field of a B.t.crop, obtaining a gut cell membrane sample from said lepidopteran, running said sample on a gel to identify an approximately 68 kDa protein band on said gel, measuring said 68 kDa protein for an amount of alkaline phosphatase enzymatic activity, and comparing said amount to a control level of alkaline phosphatase enzymatic activity determined from a gut cell membrane preparation from a control insect of known susceptibility to said Cry1 protein, wherein resistance to said Cry1 protein by said lepidopteran is indicated if said amount is less than that of a non-resistant insect, wherein said non-resistant insect is of the same genus and species as said lepidopteran.

2. The method of claim 1 wherein said enzymatic activity is measured optically.

3. The method of claim 1 wherein said Cry1 protein is Cry1Ac protein.

4. The method of claim 1 wherein said sample comprises brush border membrane vesicles (BBMV).

5. The method of claim 1 wherein said sample and said preparation comprise whole midguts from said lepidopteran and said insect.

6. The method of claim 1 wherein said Lepidoptera is of the family Noctuidae.

7. The method of claim 1 wherein said lepidotpera is a *Heliothis.*

8. The method of claim 1 wherein said lepidotpera is a *Heliothis Virescens.*

9. The method of claim 1 wherein said Cry1 protein binds an alkaline phosphatase insect receptor.

10. A kit for performing the method of claim 1, wherein said kit comprises a collection means for obtaining a gut cell membrane sample from said insect, a holding means for holding said sample, and an assaying means for assaying said sample for an altered level of an alkaline phosphatase protein, wherein an altered level of alkaline phosphatase indicates a resistant insect and an unaltered level indicates a susceptible insect.

11. The kit of claim 10 where said assaying means is a detectable substrate that undergoes enzymatic degradation in the presence of alkaline phosphatase.

12. The kit of claim 10 wherein said insect is a *Heliothis virescens* and said sample is assayed for a reduced amount of alkaline phosphatase activity.

* * * * *